(12) United States Patent
Eddaoudi et al.

(10) Patent No.: US 10,328,414 B2
(45) Date of Patent: Jun. 25, 2019

(54) HIGHLY STABLE [MAMBF6-N(O/H2O)N(LIGAND)2(SOLVENT)X]N METAL ORGANIC FRAMEWORKS

(71) Applicant: King Abdullah University of Science and Technology, Thuwal (SA)

(72) Inventors: Mohamed Eddaoudi, Thuwal (SA); Karim Adil, Thuwal (SA); Youssef Belmabkhout, Thuwal (SA); Osama Shekhah, Thuwal (SA); Prashant M. Bhatt, Thuwal (SA); Amandine Cadiau, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/564,909

(22) PCT Filed: Apr. 7, 2016

(86) PCT No.: PCT/IB2016/051992
§ 371 (c)(1),
(2) Date: Oct. 6, 2017

(87) PCT Pub. No.: WO2016/162835
PCT Pub. Date: Oct. 13, 2016

(65) Prior Publication Data
US 2018/0093250 A1     Apr. 5, 2018

Related U.S. Application Data
(60) Provisional application No. 62/144,156, filed on Apr. 7, 2015.

(51) Int. Cl.
B01J 20/22     (2006.01)
B01J 31/16     (2006.01)
(Continued)

(52) U.S. Cl.
CPC ............ B01J 20/226 (2013.01); B01D 53/02 (2013.01); B01J 20/2808 (2013.01);
(Continued)

(58) Field of Classification Search
None
See application file for complete search history.

(56) References Cited

U.S. PATENT DOCUMENTS 7,799,120 B2   9/2010   Yaghi et al.
8,926,736 B2   1/2015   Serre et al.
2015/0291870 A1  10/2015   Van Horn et al.

OTHER PUBLICATIONS

Halasyamani et al., "Syntheses and Structures of Two New Cu/Nb/pyrazine Complexes: Three Dimensional CuNb(pyz)2OF5.(pyz)(H2O) and Two Dimensional [Cu(pyz)2.5]+[NbF6]-.(pyz)". Z. anorg. allg. Chem. 622 (1996) 479-485.*
(Continued)

Primary Examiner — Daniel Berns
(74) Attorney, Agent, or Firm — Billion & Armitage; Benjamin C. Armitage

(57) ABSTRACT

Provided herein are metal organic frameworks having high selectivity and stability in the present of gases and vapors including H2S, H2O, and CO2. Metal organic frameworks can comprise metal nodes and N-donor organic ligands. Further provided are methods of making metal organic frameworks.

20 Claims, 4 Drawing Sheets

(51) Int. Cl.
B01D 53/02 (2006.01)
B01J 20/28 (2006.01)
B01J 20/30 (2006.01)
C07F 19/00 (2006.01)
C07D 241/10 (2006.01)

(52) U.S. Cl.
CPC ... *B01J 20/28061* (2013.01); *B01J 20/28071* (2013.01); *B01J 20/3078* (2013.01); *B01J 20/3085* (2013.01); *C07D 241/10* (2013.01); *C07F 19/005* (2013.01); *B01D 2253/204* (2013.01); *B01D 2256/245* (2013.01); *B01D 2257/304* (2013.01); *B01D 2257/504* (2013.01); *B01D 2258/05* (2013.01); *Y02C 10/08* (2013.01); *Y02P 20/152* (2015.11)

(56) References Cited

OTHER PUBLICATIONS

Notification of Transmittal of the International Search Report and the Written Opinion of the International Searching Authority, or the Declaration for PCT/IB/051992, dated Jun. 27, 2016.

Yang, et al., "Hydrothermal synthesis and characterization of a series of luminescent Zn(ii) and Cd(ii) coordination polymers with the new versatile m ultidentate ligand 1,3-di(1,2,4-triazol-4-yl)benzene", Crystengcomm, vol. 15, No. 40, Jan. 1, 2013, 8097.

Marvel, "Chemical Hardness and the Adaptive Coordination Behavior of the d 0 Transition Metal Oxide Fluoride Anions", Zeitschrift Fur Anorganische und Allgemeine Chemie., vol. 635, No. 6-7, May 31, 2009, 869-877.

Burd, et al., "Highly Selective Carbon Dioxide Uptake by [Cu(bpy-n)2(SiF6)] (bpy-1= 4,4'-Bipyridine; bpy-2 = 1,2-Bis(4-pyridyl)ethene)", Journal of the American Chemical Society, Feb. 8, 2012, 3663-3666.

Cadiau, et al., "Hydrothermal synthesis, ab-initio structure determination and NMR study of the first mixed Cu—Al fluorinated MOF", CrystEngComm, 2013, 3430-3435.

Couck, et al., "An Amine-Functionalized MIL-53 Metal-Organic Framework with Large Separation Power for CO2 and CH4", JACS, 2009, vol. 131, pp. 6326-6327 (published online on Apr. 17, 2009).

Dietzel, et al., "Adsorption properties and structure of CO2 adsorbed on open coordination sites of metal-organic framework Ni2(dhtp) from gas adsorption, IR spectroscopy and X-ray diffraction", ChemComm, 2008, 5125-5127.

Dietzel, et al., "Hydrogen adsorption in a nickel based coordination polymer with open metal sites in the cylindrical cavities of the desolvated framework", 2006, 959-961, (Journal: Chem. Commun.)

Ding, et al., "Hydrothermal syntheses and characterization of a series of luminescent Cd(ii) frameworks with pyridine-based and benzene-based bis-triazole ligands", Crystengcomm, vol. 15, No. 13, Jan. 1, 2013, 2490-2503.

Gautier, et al., "Orientatinal order of [VOF5]2- and [NbOF5]2- polar units in chains", Journal of Solid State Chemistry, vol. 195,, Jan. 24, 2012, 132-139.

Haisheng, et al., "Microporosity, Optical Bandgap Sizes, and Photocatalytic Activity of M(I)-Nb(V) (M = Cu, Ag) Oxyfluoride Hybrids", Crystal Growth & Design Article, vol. 10, 2010, 1323-1331.

Heier, et al., "The Polar [WO2F4]2-Anion in the Solid State", Inorg. Chem., 1999, 762-767, vol. 38.

Maggard et al., "Understanding the Role of Helical Chains in the Formation of Noncentrosymmetric Solids", J. Am. Chem. Soc., 2001, 7742-7743.

Noro, "A new methane adsorbent, porous coordination polymer [CuSiF6(4,4'-bipyridine)2]n", Angew. Chem. Int. Edition, 2000, 39, 2081-2084.

Noro, et al., "Framework Engineering by Anions and Porous Functionalities of Cu(II)/4,4¢-bpy Coordination Polymers", J. Am. Chemical Society, 2002, 124, 2568-2583.

Nugent, et al., "Enhancement of CO2 selectivity in a pillared pcu MOM platform through pillar substitution", Chem. Commun., 2013, 49, 1606--1608.

Subramanian, "Porous solids by design—[Zn(4,4'-bpy)2(SiF6)n]-xDMF, a single framework octahedral coordination polymer with large square channels", Angew. Chem. Int. Edition, 1995, 34, 2127-2129.

Vaidhyanathan, et al., "Direct Observation and Quantification of CO2 Binding Within an Amine-Functionalized Nanoporous Solid", Science, vol. 330, Oct. 29, 2010, 650-653.

Cadiau, et al., "ZnAlF5?[TAZ]: an Al fluorinated MOF of MIL-53(Al) topology with cationi {Zn(1,2,4 triazole)}2+ linkers", Journal of Materials Chemistry, 2011, p. 3949.

Mahenthirarajah, et al., "Organic-inorganic hybrid chains and layers constructed from copper-amine cations and early transition metal (Nb, Mo) oxyfluoride anions", Dalton Transaction, Jan. 1, 2009, p. 3280.

Guillory, et al., "Evidence for Nonpolar Alignment of [NbOF 5] 2—Anions in Cd(pyridine) 4 NbOF 5 Chains", Crystal Growth & Design, Feb. 1, 2006, 382-389.

Izumi, et al., "Examining the Out-of-Center Distortion in the [NbOF 5] 2—Anion", Inorganic Chemistry, Feb. 1, 2005, 884-895.

* cited by examiner

HIGHLY STABLE [MAMBF6-N(O/H2O)N(LIGAND)2(SOLVENT)X]N METAL ORGANIC FRAMEWORKS

CROSS-REFERENCE TO RELATED APPLICATIONS

This application claims priority to U.S. Provisional Application No. 62/144,156, filed 7 Apr. 2015, which application is incorporated herein by reference.

BACKGROUND

Today there is an increasing global desire to reduce greenhouse gas emissions and develop clean alternative vehicle fuels. Methane (CH4), the primary component of natural gas (NG), is of particular interest as it is abundant and has lower carbon dioxide (CO2) emission and more efficient combustion than other hydrocarbons due its high H/C ratio. Biogases, including landfill gas, are also seen as promising renewable energy resources, but, like NG, they contain significant amounts of water, CO2, and hydrogen sulfide (H2S) which must be removed before being transported, stored, and burned as a fuel. For example, NG must contain less than 1-2% CO2 and 4 ppm H2S to meet fuel gas specifications for pipeline transportation. Within many industries, gas dehydration and removal of CO2 and H2S remain some of the most intensive and challenging separations, in part due to the intolerance of many technologies to water and H2S.

Available technologies for refining NG and other biogases are often costly, multi-stage processes. Amine scrubbing is a common liquid phase system used to remove acid gases such as CO2 and H2S from NG. However, stagnant historical operating efficiencies, and the excessive oxidative degradation, evaporation, and the corrosive nature of the alkanolamine aqueous solutions create a myriad of performance, safety, and environmental concerns. Solid, porous material systems, such as zeolite and metal organic frameworks (MOFs), offer more environmentally friendly alternatives for CO2 capture, but require cumbersome, multi-stage processes. For example, zeolite has single-species selectivity for CO2 and cyclic adsorption performance in the presence of moisture that require prior dehydration and H2S removal stages. MOFs, similarly, can be designed for CO2 capture, but most MOF structures reported so far exhibit prohibitively low stability for water and H2S.

MOFs generally include porous crystals which are assembled from modular molecular building blocks, and provide a wide array of advantageous material properties, including high surface area, porosity, stability, and sorption potential. While the available building block options, and combinations thereof, are virtually limitless, such potential highlights the statistical difficulty in identifying and assembling MOFs with desired and particularized material properties.

SUMMARY

In general, this disclosure describes porous metal organic frameworks (MOFs). This disclosure describes a new platform of MOF materials with outstanding stability with intrinsic properties that could be potentially suitable for the capture and removal of gases and/or vapors from fluids. In particular, this disclosure provides MOFs with outstanding stability to water and H2S. It should be noted that the embodiments of this disclosure are further generally applicable to many fields including gas molecule separation, gas storage, catalysis, sensors, drug delivery, rare gas separation, and proton conductivity.

In one embodiment, a MOF can be characterized by the formula MaMbF6-n(O/H2O)n(Ligand)2(solvent)x, wherein Ma comprises elements selected from periodic groups IB, IIA, IIB, IIIA, IVA, IVB, VIB, VIIB, and VIII, Mb comprises elements selected from periodic groups IIIA, IIIB, IVB, VB, VIB, and VIII, Ligand comprises an organic, poly-functional, N-donor ligand, and n is at least equal to 1.

In one embodiment, a method of synthesizing a MOF comprises combining reactants sufficient to form a mixture, reacting the mixture over a period of time sufficient to form a reacted mixture, and processing the reacted mixture to provide a metal organic framework.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

Figure 1B:
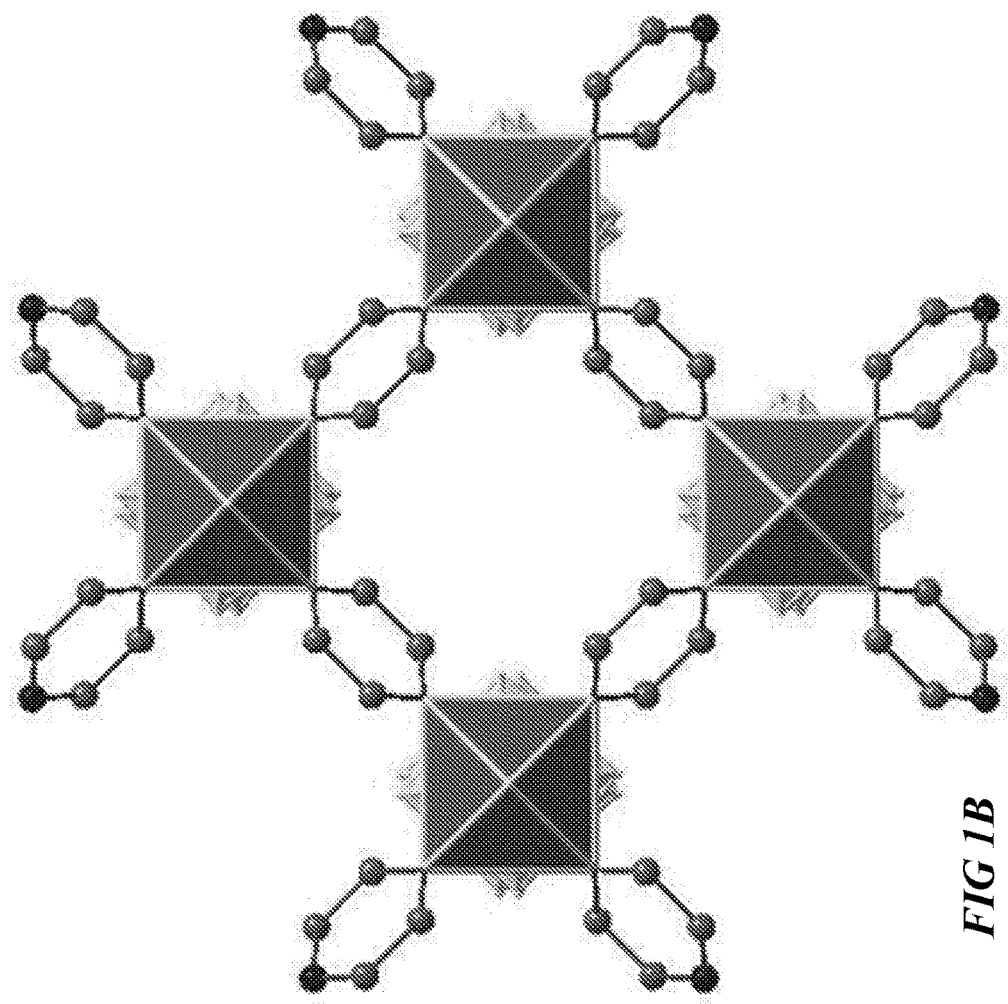
FIG. 1B illustrates a schematic view of a metal organic framework, according to one or more embodiments of this disclosure.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As used herein, "fluids" can refer to a gas, liquid, or combination thereof. A gas or liquid can include one or more components. For example, a fluid can include a gas stream comprising $CO_2$, $H_2S$ and water vapor.

As used herein, "refining" refers to removing one or more unwanted components or separating one or more components from remaining components of a composition, such as a fluid. For example, refining can include removing a fraction of $H_2S$ from a fluid, such as natural gas.

As used herein, "poly-functional" refers to the characteristic of having more than one reactive or binding sites. For example, a poly-functional ligand can attach to a metal ion in multiple ways, bridge multiple metal ions, or combinations thereof. Specifically, pyrazine is a poly-functional ligand.

As used herein, "water" or "H2O" can include solid, liquid, or vapor phases.

Gas storage and separation using porous materials has experienced significant development in recent years in various industrial applications related to energy, environment, and medicine. Among porous materials, metal organic frameworks (MOFs) are a versatile and promising class of crystalline solid state materials which allow porosity and functionality to be tailored towards various applications. MOF crystal chemistry uses a molecular building block (MBB) approach that offers potential to construct MOFs where desired structural and geometrical information are incorporated into the building blocks prior to the assembly process.

Generally, MOFs comprise a network of nodes and ligands, wherein a node has a connectivity capability at three or more functional sites, and a ligand has a connectivity capability at two functional sites each of which connect to a node. Nodes are typically metal ions or metal containing clusters, and, in some instances, ligands with node connectivity capability at three or more functional sites can also be characterized as nodes. In some instances, ligands can include two functional sites capable of each connecting to a node, and one or more additional functional sites which do not connect to nodes within a particular framework. A MBB can comprise a metal-based node and an organic ligand which extrapolate to form a coordination network. Such coordination networks have advantageous crystalline and porous characteristics affecting structural integrity and interaction with foreign species (e.g., gases). The particular combination of nodes and ligands within a framework will dictate the framework topology and functionality. While essentially limitless combinations of nodes and ligands exist, to date, very few MOF materials are $H_2S$ stable which consequently preclude their use in separation of gases containing even traces of $H_2S$.

As disclosed in co-owned U.S. Application No. 62/044,928, a series of isoreticular MOFs with periodically arrayed hexafluorosilicate (SiF6) pillars, called SIFSIX-2-Cu-i and SIFSIX-3-Zn, SIFSIX-3-Cu and SIFSIX-3-Ni showed particularly high $CO_2$ selectivity and capture. These properties in SIFSIX-3-M materials suggest broad applications from ppm level $CO_2$ removal to bulk $CO_2$ separation. However, with the exception of SIFSIX-3-Ni, the SIFSIX-3-M materials were not tolerant to $H_2S$. And although these materials exhibit high structural stability in the presence of $CO_2$, extensive exposure of all SIFSIX-3-M materials to moisture detrimentally induces a phase change and the formation of new 2D stable materials. These 2D materials exhibit relatively unaltered selectivity but diminished $CO_2$ uptake. This indicates that the SIFSIX-3-M materials series is not sufficiently robust to handle $CO_2$ and $H_2S$ capture in most critical applications throughout the oil and gas and renewable fuels industries, especially in applications which bring the materials into contact with moisture and $H_2S$.

Provided herein are novel functionalized MOFs suitable for a myriad of applications, which exhibit high water vapor and $H_2S$ tolerance and stability over thousands of cycles. For example, efficiency of $H_2S$ and $CO_2$ separation is enhanced, in part, by the stability of these MOFs in the presence of water and $H_2S$. These MOFs eliminate the safety, efficiency, and environmental concerns associated with amine scrubbing techniques while providing high stability in the presence of water and $H_2S$. The benefits of this innovative approach include the following: (i) no environmental and safety hazards germane to amine scrubbing (ii) no preliminary separate desulfurization is necessary (iii) no separate gas drying is needed, and (iv) no compression-decompression/cooling of NG is required. Further, the MOFs provided herein offer exceptional thermal and mechanical stability, particularly during adsorption/desorption.

MOFs, as provided herein, comprise one or more MBBs. Generally, a MBB, or a network of MBBs, can be represented by the formula $[(node)_a(ligand)_b(solvent)_c]_n$, wherein n represents the number of molecular building blocks. Solvent represents a guest molecule occupying pores within the MOF, for example as a result of MOF synthesis, and can be evacuated after synthesis to provide a MOF with unoccupied pores. Accordingly, the value of c can vary down to zero, without changing the definitional framework of the MOF. Therefore, in many instances, MOFs as provided herein can be defined as $[(node)_a(ligand)_b]_n$, without reference to a solvent or guest molecule component.

In some embodiments herein, MOFs can be characterized by the formula $[M_aM_bF_{6-n}(O/H_2O)_w(Ligand)_x(solvent)_y]_z$. In some embodiments, solvent can include a chemical species present after fabrication of the MOF. In some embodiments, solvent can include a functionalizing guest molecule, such as water, dimethylformamide (DMF), diethylformamide (DEF), and alcohols, among others. Some embodiments herein comprise a porous, uninhabited MOF characterized by the formula $[(node)_a(ligand)_b]_n$, wherein node comprises, generally, $M_aM_bF_xO_y(O/H_2O)_z$. In some embodiments, Ma comprises elements selected from periodic groups IB, IIA, IIB, IIIA, IVA, IVB, VIB, VIIB, or VIII. In some embodiments, Mb comprises elements selected from periodic groups IIIA, IIIB, IVB, VB, VIB, or VIII. In some embodiments, Ma comprises elements selected from periodic groups IB, IIA, IIB, IIIA, IVA, IVB, VIB, VIIB, or VIII and Mb comprises elements selected from periodic groups IIIA, IIIB, IVB, VB, VIB, or VIII.

In some embodiments, Ma can comprise one of the following cations: Cu2+, Zn2+, Co2+, Ni2+, Mn2+, Zr2+, Fe2+, Ca2+, Ba2+, Pb2+, Pt2+, Pd 2+, Ru2+, Rh2+, Cd2+, Mg+2, Al+3, Fe+2, Fe+3, Cr2+, Cr3+, Ru2+, Ru3+ and Co3. In some embodiments, Mb can be one of the following Al+3, Fe+2, Fe+3, Cr2+, Cr3+, Ti3+, V3+, V5+, Sc3+, In3+, Nb5+, Y3+. In some embodiments, Ma can comprise one of the following cations: Cu2+, Zn2+, Co2+, Ni2+, Mn2+, Zr2+, Fe2+, Ca2+, Ba2+, Pb2+, Pt2+, Pd 2+, Ru2+, Rh2+, Cd2+, Mg+2, Al+3, Fe+2, Fe+3, Cr2+, Cr3+, Ru2+, Ru3+ and Co3; Mb can be one of the following Al+3, Fe+2, Fe+3, Cr2+, Cr3+, Ti3+, V3+, V5+, Sc3+, In3+, Nb5+, Y3+. In such embodiments, the ligand can be any bi-functional N-donor linkers based on monocyclic or polycyclic group (aromatic or not).

In some embodiments, a ligand can comprise a polydentate, or poly-functional ligand, such as a bi-functional ligand, a tri-functional ligand, or ligands with four or more functional sites. In some embodiments, a ligand can comprise an N-donor linker. In some embodiments a ligand can comprise a poly-functional ligand. In some embodiments, a ligand can comprise a plurality of N-donor functional groups. In some embodiments, a ligand can comprise a monocyclic or polycyclic group structure, wherein the cyclic groups can be aromatic or non-aromatic. In some embodiments, a ligand can comprise a nitrogen-containing monocyclic or polycyclic group structure. In some embodiments, a ligand can comprise a nitrogen-containing heterocyclic ligand, including pyridine, pyrazine, pyrimidine, pyridazine, triazine, thiazole, oxazole, pyrrole, imidazole, pyrazole, triazole, oxadiazole, thiadiazole, quinoline, benzoxazole, benzimidazole, and tautomers thereof.

Some embodiments of suitable MOFs can be represented by the following general formula:

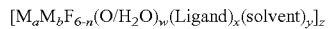

wherein $M_a$ can be one of the following cations: Cu2+, Zn2+, Co2+, Ni2+, Mn2+, Zr2+, Fe2+, Ca2+, Ba2+, Pb2+, Pt2+, Pd 2+, Ru2+, Rh2+, Cd2+, Mg+2, Al+3, Fe+2, Fe+3, Cr2+, Cr3+, Ru2+, Ru3+ and Co3; $M_b$ can be one of the following Al+3, Fe+2, Fe+3, Cr2+, Cr3+, Ti3+, V3+, V5+, Sc3+, In3+, Nb5+, Y3+; and the ligand can be any bi-functional N-donor linkers based on monocyclic or polycyclic group, aromatic or not.

Figure 1A:
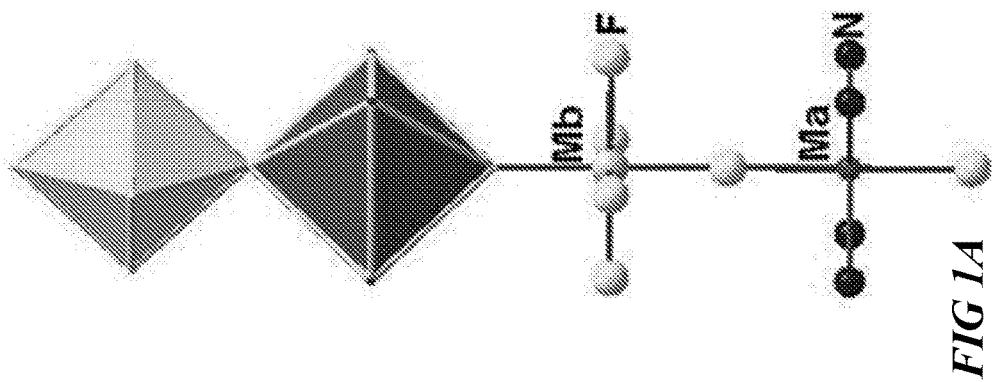
FIG. 1A illustrates a schematic of an inorganic chain, according to one or more embodiments of this disclosure.

One MOF synthesis strategy provided herein comprises linking inorganic chains using appropriate N-donor based linkers to deliberately generate channels along one crystallographic direction. The inorganic chains are built up from the trans-connection between $M_aN_4F_2$ and $M_bF_4(H_2O)_2$ octahedra or between $M_aN_4F_2$ and $M_bF_5(H_2O)$ octahedra or between $M_aN_4F_2$ octahedra and $M_bF_5(O)$ octahedra. FIG. 1A illustrates an example of an inorganic chain, built up from $M_aN_4F_2$ and $M_bF_5(H_2O)$ octahedra. The resulted inorganic chains are linked to each other using bi-functional N-donor organic ligands, thereby generating channels with different sizes and shapes depending on the nature of the organic linker. FIG. 1B illustrates a schematic view of one embodiment of a MOF comprising a $NiNbF_5O(pyrazine)_2$ structure, viewed along the c-axis.

The novel series of MOFs structures disclosed herein can be designed with a variety of pore sizes and/or open-metal sites which afford tunable properties for a variety of applications, particularly due to a high stability in the presence of water vapor and H2S. Tuning, in some embodiments, can include modification of the organic and/or inorganic components of the MOF. For example, in some embodiments, lighter metal-based clusters can be used to lower the framework density and increase the relative wt. % of captured CO2 and/or H2S. Further, the MOF platforms as provided herein allow for an unprecedented high degree of tuning control at the molecular level, allowing the size and shape of channels within a MOF architecture to be rigorously controlled and adapted to specific separation of numerous gases, even beyond water vapor and H2S.

The utility of MOFs such as those provided herein are highly dependent upon the framework's structural features such as structural strength, density, functionality, pore aperture dimensions, pore dimensions, the ratio of pore aperture dimensions to pore dimensions, pore accessibility, and the presence of a plurality of pore dimensions and/or pore aperture dimensions (e.g., a poly-porous MOF). Because the MOFs provided herein are highly tunable, the potential for utility is vast.

The originality of this new class of crystalline porous materials is based, in part, on the fact that the shape of cavities, (i.e. square or rectangle based channels), is controlled from a structural point of view using appropriate cations and organic linkers. The novel MOF architectures disclosed herein offer a novel improvement on some MOF architectures by replacing silicon components with other metals, such as Al3+, Fe2+, Fe3+, V3+, V4+, V5+, Nb5+, to afford highly stable materials with or without open metals sites. In some embodiments, the use of specific cations, such as Al+3, Fe+2, Fe+3, Cr2+, Cr3+, Ti3+, V3+, V5+, Sc3+, In3+, Y3+, in Mb site positions can introduce open-metal sites within the channels that enhance properties of stability, for example.

In some embodiments, a representative $[M_aM_bF_{6-n}(O/H_2O)_w(Ligand)_x(solvent)_y]_z$ MOF structure can include a Ni $M_a$ constituent, an $M_b$ constituent group selected from one of Al, Fe, V, or Nb, and a Ligand comprising a pyrazine constituent group. All such embodiments offer high affinity and stability to water vapor and $H_2S$, unlike the Cu and Zn-based analogues of SIFSIX-3-M materials made with Si. In in some embodiments a MOF characterized by the formula $[M_aM_bF_{6-n}(O/H_2O)_w(Ligand)_x(solvent)_y]_z$ wherein $M_a$ equals Ni, $M_b$ equals Al, Fe, V or Nb, and ligand equals pyrazine, the pore size (channel size) of the resulting MOF can be about 3.3 Å to about 3.8 Å, or about 2.8 Å to about 4.8 Å. In some embodiments, the channels are square/rectangular. In the same or in an alternative embodiment, a MOF can have a specific surface area of about 250 m2/g to about 500 m2/g. In either of the same MOFs or in an alternative embodiment, a MOF can have a pore volume of about 0.1 cm3/g to about 0.25 cm3/g. In a different embodiment, a more elongated ligand can provide an analogous MOF with much higher porosity.

In some embodiments, $M_b$ and/or a ligand can be selected to hinder or allow rotation of a ligand. Altering the nature, shape, and dimensions of the $(M_bOF_5)^{x-}$ pillars employed in $[M_aM_bF_{6-n}(O/H_2O)_w(Ligand)_x(solvent)_y]_z$ MOFs can selectively hinder the free rotation of ligands and thus dictate the maximum and/or minimum opening of the pore aperture size. This approach offers potential to dial-in/command the passing-blocking of specific probe molecules. In some embodiments $M_b$ and/or a ligand are selected to allow no rotation of a ligand. In some embodiments $M_b$ and/or a ligand are selected to allow full rotation of a ligand. In some embodiments $M_b$ and/or a ligand are selected to allow partial rotation of a ligand.

In some embodiments, $M_b$ and/or a ligand can be selected to hinder or allow rotation of a pillar. Altering the nature, shape, and dimensions of the $(M_bOF_5)^{x-}$ pillars employed in $[M_aM_bF_{6-n}(O/H_2O)_w(Ligand)_x(solvent)_y]_z$ MOFs can selectively hinder the free rotation of pillars and thus dictate the maximum and/or minimum opening of the pore aperture size. This approach offers potential to dial-in/command the passing-blocking of specific probe molecules. In some embodiments $M_b$ and/or a ligand are selected to allow no rotation of a pillar. In some embodiments $M_b$ and/or a ligand are selected to allow full rotation of a pillar. In some embodiments $M_b$ and/or a ligand are selected to allow partial rotation of a pillar.

In some embodiments, $M_b$ and/or a ligand can be selected to hinder or allow rotation of a ligand and a pillar. Altering the nature, shape, and dimensions of the $(M_bOF_5)^{x-}$ pillars employed in $[M_aM_bF_{6-n}(O/H_2O)_w(Ligand)_x(solvent)_y]_z$ MOFs can selectively hinder the free rotation of a ligand and a pillar and thus dictate the maximum and/or minimum opening of the pore aperture size. This approach offers potential to dial-in/command the passing-blocking of specific probe molecules. In some embodiments $M_b$ and/or a ligand are selected to allow no rotation of a ligand and a pillar. In some embodiments $M_b$ and/or a ligand are selected to allow full rotation of a ligand and a pillar. In some embodiments $M_b$ and/or a ligand are selected to allow partial rotation of a ligand and a pillar.

A specific MOF characterized by the formula $[M_aM_bF_{6-n}(O/H_2O)_w(Ligand)_x(solvent)_y]_z$ is NbOFFIVE-1-Ni, wherein $M_a$ comprises Ni and $M_b$ comprises Nb. This MOF includes a $(NbOF_5)^{2-}$ inorganic pillar which, due to the larger $Nb^{+5}$, has a longer Nb—F bond length (1.905(1) Å) as compared to the Si—F bond length (1.681(1) Å) of the SIFSIX MOFs described above. The increased Nb—F bond length reduces the distance between the pendant fluorine in the channel, and the relatively increased nucleophile behavior of $(N_bOF_5)^{2-}$ provides increased stability in the presence of water. Pyrazine is a suitable ligand for the NbOFFIVE-1-Ni MOF, among others as described herein. NbOFFIVE-1-Ni is a pillared sql-MOF based on $(NbOF_5)^{2-}$ pillars that connect a 2D square grid of Ni-(pyrazine)$_2$. The quadrangular-pillared sql-MOF can be viewed as a 3D MOF wherein each NiOF (pyrazine)$_4$ node serves as 6-connected node connected by $(NbOF_5)^{2-}$ pillars through fluorine/oxygen atoms giving rise to a pcu topology. It must be noted that the assignment of one oxygen and one fluorine atom in apical position within the pillar has been previously demonstrated in similar materials and confirmed with supporting techniques.[12] The overall framework consists of square shaped open channels having slightly smaller diameters of about 3.175(1) Å (taking account of van der Walls radii) comparatively to the analogue material SIFSIX-3-Cu (3.980(1) Å).

A specific MOF characterized by the formula $[M_aM_bF_{6-n}(O/H_2O)_w(Ligand)_x(solvent)_y]_z$ is AlFFIVEH$_2$O-1-Ni, wherein $M_a$ comprises Ni and $M_b$ comprises Al. When utilizing a pyrazine ligand, this MOF can be characterized by the specific formula NiAlF$_5$(H$_2$O)(pyr)$_2$.2H$_2$O, although other ligands described herein can be suitable. Another specific MOF characterized by the formula $[M_aM_bF_{6-n}(O/H_2O)_w(Ligand)_x(solvent)_y]_z$ is FeFFIVEH$_2$O-1-Ni, wherein $M_a$ comprises Ni and $M_b$ comprises Fe. When utilizing a pyrazine ligand, this MOF can be characterized by the specific formula NiFeF$_5$(H$_2$O)(pyr)$_2$.4H$_2$O, although other ligands described herein can be suitable. AlFFIVEH$_2$O-1-Ni and FeFFIVEH$_2$O-1-Ni are isomorphs, and take advantage of the periodically arrayed fluorine combined with the adequate one dimensional channel size. In contrast to the Si of SIFSIX MOFs described above, the introduction of open metal sites within the framework is concomitant with the utilization of an appropriate metal with the required oxidation state that allows the presence of a water molecule within the metal coordination sphere. Aluminum and Iron cations were used such that the MOF would adopt an octahedral fluorinated environment and lead to open metal sites after coordinated water removal via proper activation. Each isomorph utilizing pyrazine as a ligand exhibits a primitive cubic (pcu) topology resulting from the pillaring of metal-pyrazine 2D square-grid moieties with $(MF_5H_2O)^{2-}$ ($M=Al^{3+}$ or $Fe^{3+}$) inorganic pillars. [Consider including FIG. 1 from NiAl Natmater 8march to show MOF structure]

Although AlFFIVEH$_2$O-1-Ni and FeFIVEH$_2$O-1-Ni are isomorphs to the SiFSIX MOFs described above, the replacement of Si(IV) by Al(III) or Fe(III) is impossible using similar methods for synthesizing SIFSIX materials which utilize NiSiF$_6$ as a cation source. Because no equivalent starting material for Al(III) and Fe(III) exist, new experimental reactions conditions as described in Examples 2-4 were developed in order to hydrothermally synthesize these two novel fluorinated MOFs in highly acidic solution.

Figure 2:
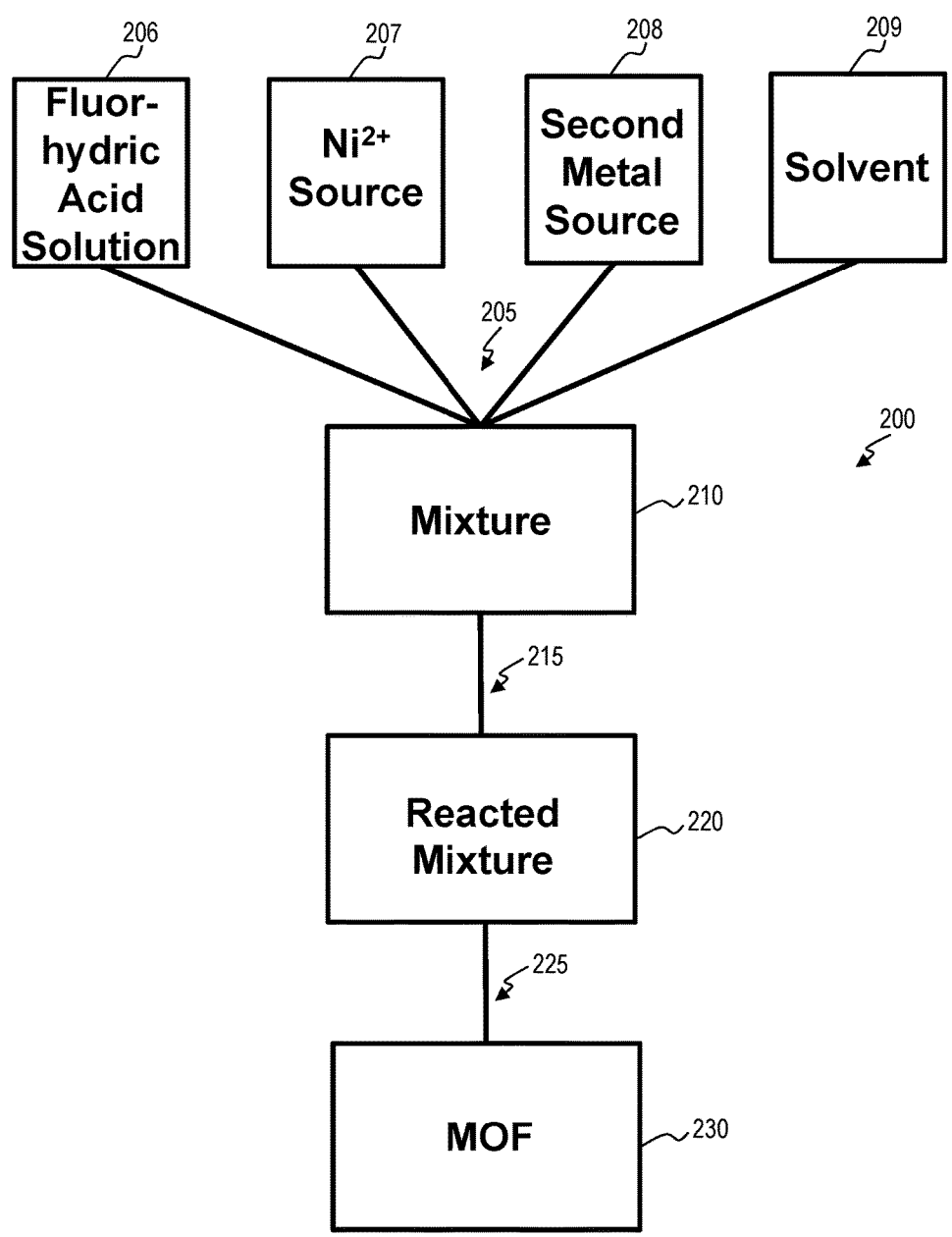
FIG. 2 illustrates a method of fabricating a metal organic framework, according to one or more embodiments of the disclosure.

Some such MOFs can be fabricated using a solvo(hydro) thermal synthetic procedure. As shown in FIG. 2, a method for fabricating 200 a MOF 230 can include combining 205 reactants. Reactants can include one or more of a fluorhydric acid solution 206 with a Ni2+ source 207, a second metal source 208, and a solvent 209 to form a mixture 210. A Ni2+ source 207 can include one or more of nickel nitrate, hydrated nickel nitrate, nickel chloride, hydrated nickel chloride, nickel fluoride, hydrated nickel fluoride, nickel oxide, or hydrated nickel oxide. The second metal source 208 can include an Al+3 source, an Fe+2 source, an Fe+3 source, a Cr2+ source, a Cr3+ source, a Ti3+ source, a V3+ source, a V5+ source, a Sc3+ source, an In3+ source, a Nb5+ source, a Y3+ source, for example. These, metals can be in the form of nitrates, hydrated nitrates, chlorides, hydrated chlorides, fluorides, hydrated fluorides, oxides, hydrated oxides, and combinations thereof. The solvent 209 can include one or more of H$_2$O, DMF, and DEF. The method for fabricating 200 can further comprise allowing the mixture 210 to react 215, sufficient to form a reacted mixture 220. Reacting 215 can include one or more of contacting the fluorhydric acid solution 206, the Ni2+ source 207, the second metal source 208, and the solvent 209, stirring or agitating the mixture 210, or heating the mixture 210. Heating the mixture 210 can comprise heating to a temperature between about 80° C. to about 200° C. The reacted mixture 220 can be further processed 225 to provide a fabricated MOF 230. Processing 220 can include one or more of filtering the reacted mixture 220, rinsing the reacted mixture 220 with water, removing excess reactants from the reacted mixture 220. In some embodiments, guest molecules are optionally evacuated from a fabricated MOF 230. Guest molecules can include solvent guest molecules, or derivatives thereof.

Figure 3A:
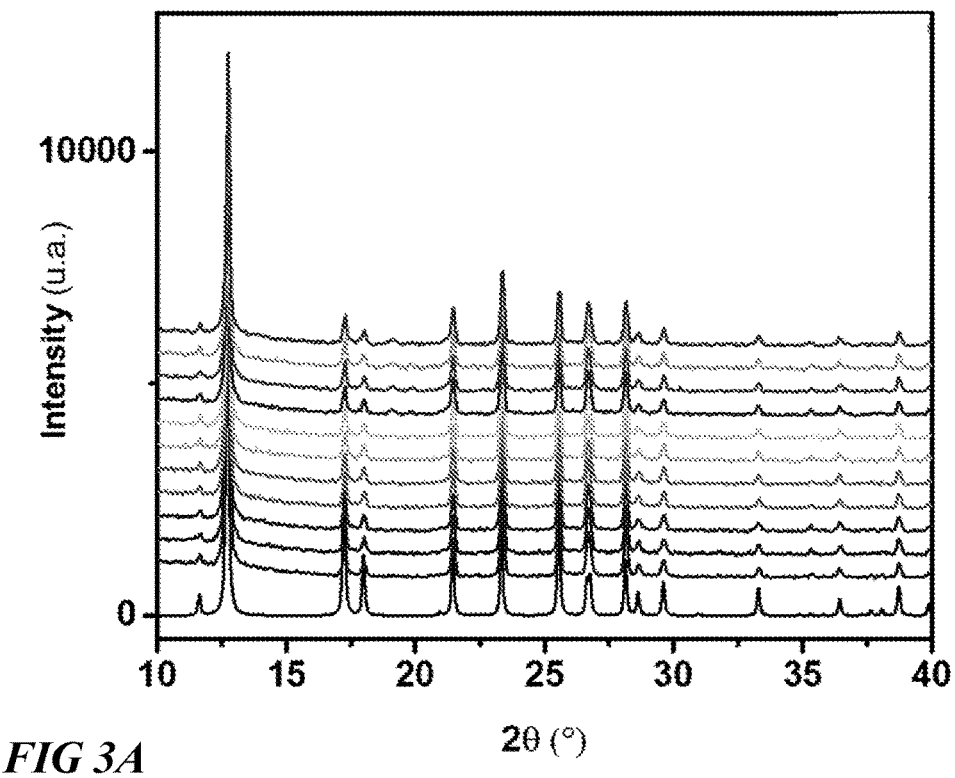
FIG. 3A illustrates powder X-ray diffraction data of a metal organic framework, according to one or more embodiments of this disclosure.
Figure 3B:
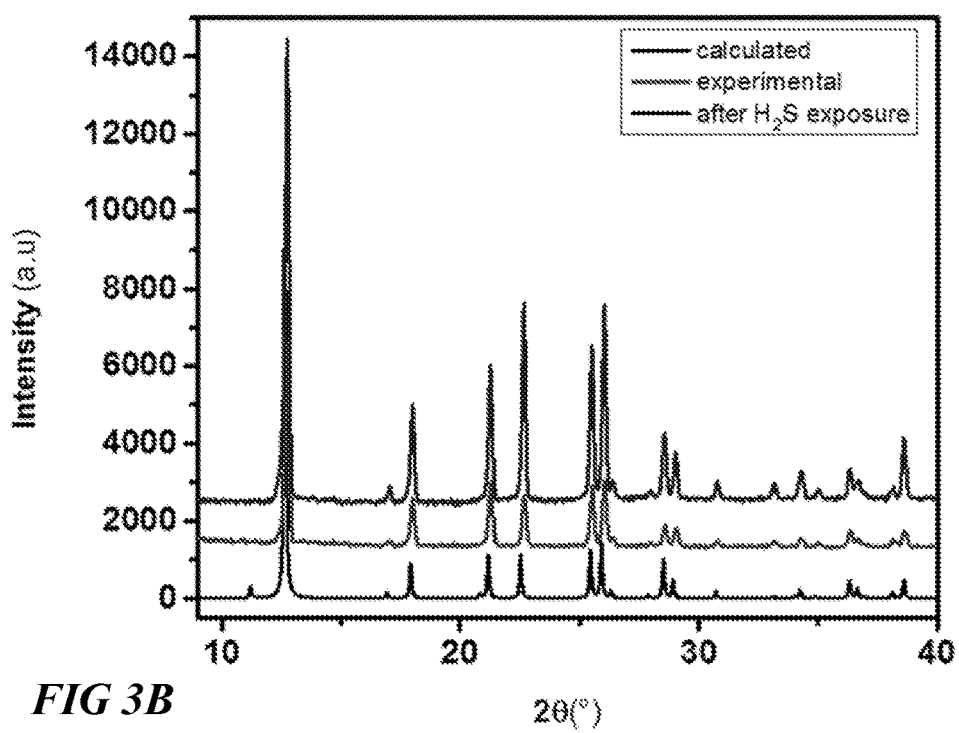
FIG. 3B illustrates powder X-ray diffraction data of a metal organic framework, according to one or more embodiments of this disclosure.

In one embodiment, a representative $[M_aM_bF_{6-n}(O/H_2O)_w(Ligand)_x(solvent)_y]_z$ MOF structure can include a Ni Ma constituent, a Nb Mb constituent group, and a ligand comprising a pyrazine constituent group. FIG. 3A illustrates powder X-ray diffraction data of this MOF, characterized by the formula NiNbF$_5$O(pyrazine)$_2$(solvent)$_y$, confirming the high stability of the MOF in the presence of water. FIG. 3B illustrates powder X-ray diffraction data of this MOF, confirming the high stability of the MOF in the presence of H2S.

In some embodiments, one or more MOFs described herein are suitable for applications involving gas/vapor/solvent dehydration. The particular outstanding properties of $[M_aM_bF_{6-n}(O/H_2O)_w(Ligand)_x(solvent)_y]_z$ as compared to SIFSIX-3-M (Cu, Zn, Ni) materials, as well as others known in the art, in terms of stability to moisture, H2O uptake and affinity make these series of novel MOFs suitable for many industrial application where various degrees of humidity need to be removed. Furthermore, these materials are advantageous in that exposure to moisture in non-process settings (e.g., transport, installation, maintenance, etc.) will not affect performance. For example, MOFs, with and without open metal sites, characterized by the formula $[M_aM_bF_{6-n}(O/H_2O)_w(Ligand)_x(solvent)_y]_z$, exhibit a number advantageous of $CO_2$ properties (e.g., gas uptake, gas selectivity, kinetics) at various humidity conditions (e.g., up to ca. 100% relative humidity.)

These and other results can be expected in similar other embodiments, with or without open metal sites, such as MOF structure characterized by the formula NiMbF5O(pyrazine)2, wherein Mb can be one of the following Al+3, Fe+2, Fe+3, Cr2+, Cr3+, Ti3+, V3+, V5+, Sc3+, In3+, Nb5+, Y3+. These and other results can be expected in similar other embodiments, with or without open metal sites, such as MOF structure characterized by the formula $M_aN_bF_5O(pyrazine)_2$, wherein Ma can be one of the following cations: Cu2+, Zn2+, Co2+, Ni2+, Mn2+, Zr2+, Fe2+, Ca2+, Ba2+, Pb2+, Pt2+, Pd 2+, Ru2+, Rh2+, Cd2+, Mg+2, Al+3, Fe+2, Fe+3, Cr2+, Cr3+, Ru2+, Ru3+.

Example 1: Aperture Size Modification

Figure 4A:
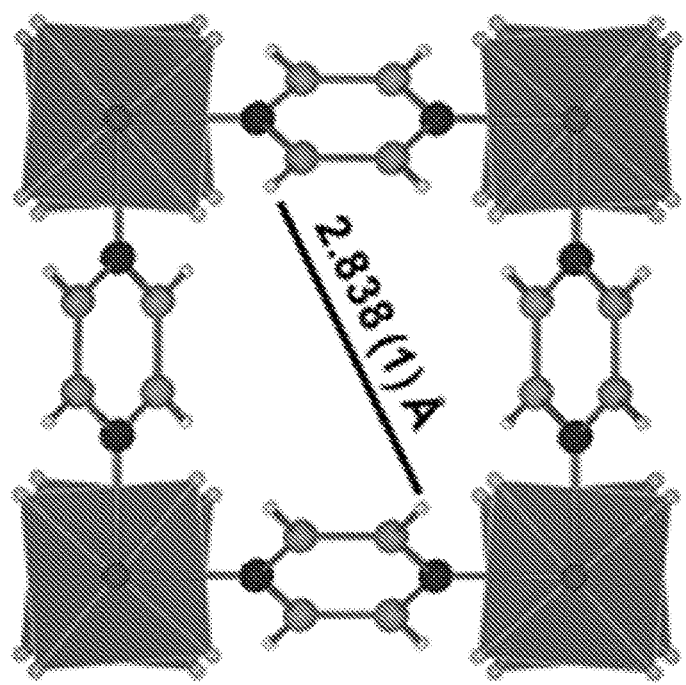
FIG. 4A illustrates a restricted pore aperture of an NbOFFIVE-1-Ni MOF, according to one or more embodiments of this disclosure.
Figure 4B:
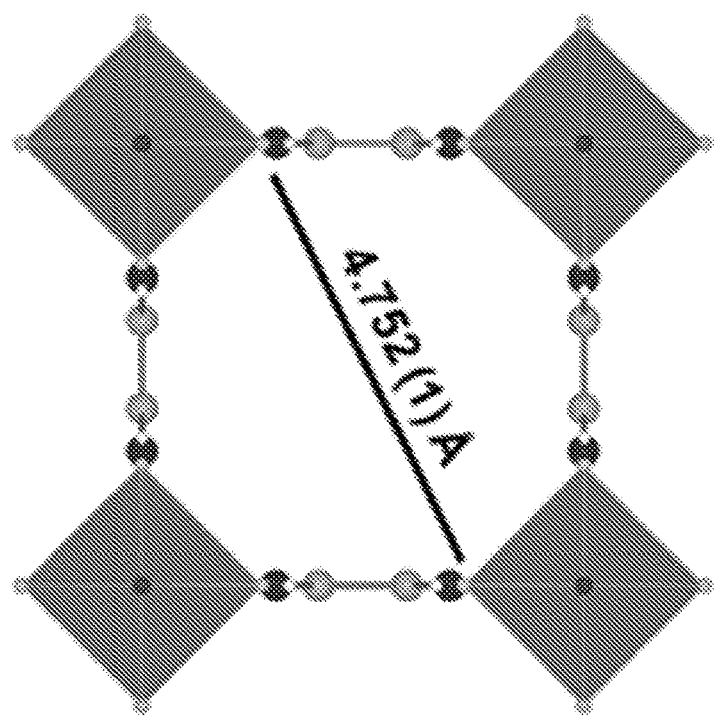
FIG. 4B illustrates an expanded pore aperture of an NbOFFIVE-1-Ni MOF, according to one or more embodiments of this disclosure.

Altering the nature, shape, and dimensions of the pillars employed in $[M_aM_bF_{6-n}(O/H_2O)_w(Ligand)_x(solvent)_y]_z$ MOFs can selectively hinder the free rotation of ligands and thus dictate the maximum and/or minimum opening of the pore aperture size. This approach offers potential to dial-in/command the passing-blocking of specific probe molecules. The $(NbOF_5)^{2-}$ pillaring inorganic building block of NbOFFIVE-1-Ni utilizing a pyrazine ligand demonstrates this approach. Analysis of the NbOFFIVE-1-Ni structure (collected at 100K) revealed the plausible smallest pore window opening associated with the relatively hindered rotation of the $(NbOF_5)^{2-}$ pillars and the presence of hydrogen bond interactions. As a result, the hydrogen atoms of the pyrazine linkers circumference the resultant rectangular aperture size of 2.838(1) Å, as shown in FIG. 4A, prohibiting the diffusion of any molecule other than water. In order to gain a better insight on the plausible rotation and tilting of the pyrazine linker and subsequently derive a relative maximum opening of the window, providing a gate limit for the largest molecule to pass through, the same structure was collected and analysed at room temperature. Noticeably, at room temperature, the pyrazine molecules are perceived to freely rotate along the N . . . N axis, while the $(NbOF_5)^{2-}$ pillars rotate along the 4-fold axis, as shown in FIG. 4B. The concurrent pyrazine and pillars $(NbOF_5)^{2-}$ mobility afforded a maximum window aperture size of 4.752(1) Å.

Example 2: Synthesis of NbOFFIVE-1-Ni

A NbOFFIVE-1-Ni MOF was synthesized via a solvothermal reaction utilizing a hydrofluoric acid solution of a mixture of $Ni(NO_3)_2 6H_2O$, $Nb_2O_5$, and pyrazine. The reaction yielded violet, square shaped crystals of $NiNbOF_5(pyrazine)_2.2H_2O$ which are referred to as NbOFFIVE-1-Ni. Single crystal X-ray diffraction of a single NbOFFIVE-1-Ni crystal at 100K revealed that the MOF crystallized in tetragonal space group I4/mcm with unit cell parameters a=b=9.8884(4) Å and c=15.783(1) Å. High thermal stability of the material was confirmed by variable-temperature PXRD performed in the range of 25° C. to 400° C., establishing that the material retains its crystallinity over the temperature range. The water stability of the material was also confirmed via in-situ variable-humidity PXRD up to 95% humidity. Moreover, excellent tolerance to hydrogen sulfide, a feature that is rarely proven for MOFs, was demonstrated by PXRD after exposure to $H_2S$ and by collecting adsorption isotherms of $H_2S$. Nitrogen adsorption isotherm at 77K performed on activated material indicated that NbOFFIVE-1-Ni is not porous to $N_2$. Consequently, adsorption investigation was carried out using smaller probe molecule than $N_2$, such as $CO_2$ (at 273 K) to verify the porous nature of material. The BET specific surface area and pore volume as determined from $CO_2$ adsorption at 273 K is 280 m²/g and 0.095 cm³/g, respectively.

Example 3: Synthesis of $AlFFIVEH_2O$-1-Ni

An $AlFFIVEH_2O$-1-Ni MOF characterized by the formula $NiAlF_5(H_2O)(pyr)_2.2H_2O$ was synthesized by mixing pyrazine (0.3844 g, 4.8 mmol, Aldrich), $NiNO_3$ (0.1745 g, 0.6 mmol, Acros), $Al(NO_3)_3$ (0.225 g, 0.6 mmol) and $HF_{aq}$ 48% (0.255 ml, 6 mmol) and dispersing the mixture in deionized water in a 100 ml Teflon liner. The mixture was placed in an autoclave, and the autoclave was then sealed and heated to 85 C.° for 24 h. After cooling down, the resulting blue-violet square shape crystals, suitable for single crystal structure determination, were separated by filtration, washed with ethanol and dried in air. N=13.76% (theo. 14.19%), C=21.73% (theo. 24.33%), H=3.16% (theo. 3.57%). $AlFFIVEH_2O$-1-Ni was activated at 95° C. for one night under high vacuum (3 milliTorrs) before every sorption measurements. All reagents were used as received from commercial suppliers without further purification.

Single-crystal diffraction experiments revealed that the MOF crystallized in tetragonal space group I4/mcm. High thermal stability of the material was confirmed by variable-temperature PXRD performed up to 400° C., establishing that the material retains its crystallinity over a broad temperature range. The water stability of the material was also confirmed via in-situ variable-humidity PXRD up to 95% humidity relative to calculated theoretical values.

Crystallographic studies revealed the presence of $(AlF_5(H_2O))^{2-}$ inorganic building blocks within the framework acting as pillars. In addition to water molecules connected to aluminium, thermogravimetric analysis confirmed the presence of water molecules located within the channels. The investigation of the electron density within the cavities revealed two crystallographic independent water molecules present within the cavities of $AlFFIVEH_2O$-1-Ni. A hydrogen bond network between fluorine atoms of pillars and water guest molecules was revealed, with the symmetrically generated water molecules connected to each other and to fluorine atoms belonging to the pillars. It must be noted that water molecules from the pillar are also part of the network.

Example 4: Synthesis of $FeFFIVEH_2O$-1-Ni

An $FeFFIVEH_2O$-1-Ni MOF characterized by the formula $NiFeF_5(H_2O)(pyr)_2.4H_2O$ was synthesized by mixing pyrazine (0.3844 g, 4.8 mmol, Aldrich), $Ni(NO_3)_2$ (0.1745 g, 0.6 mmol, Acros), $Fe(NO_3)_3$ (0.2323 g, 0.6 mmol) and $HF_{aq}$ 48% (0.255 ml, 6 mmol) and dispersing the mixture in deionized water (3 ml) in a 100 ml Teflon liner. The mixture was placed in an autoclave, and the autoclave was then sealed and heated to 85 C.° for 24 h. After cooling down, the resulting blue square shape crystals, suitable for single crystal structure determination, were separated by filtration, washed with ethanol and dried in air. Notice that sometimes only light blue powder is obtained. Elemental analysis: N=11.79% (theo. 12.19%), C=20.24% (theo. 20.90%), H=3.53% (theo. 3.95%), O=17.13% (theo. 17.40%). $FeFFIVEH_2O$-1-Ni was activated at 95° C. for one night under high vacuum (3 milliTorr) before every sorption measurements. All reagents were used as received from commercial suppliers without further purification.

Single-crystal diffraction experiments revealed that the MOF crystallized in tetragonal space group P4/nbm. High thermal stability of the material was confirmed by variable-temperature PXRD performed up to 250° C., establishing that the material retains its crystallinity over a broad temperature range. The water stability of the material was also confirmed via in-situ variable-humidity PXRD up to 95% humidity relative to calculated theoretical values.

Crystallographic studies revealed the presence of $(FeF_5(H_2O))^{2-}$ inorganic building blocks within the framework acting as pillars. In addition to water molecules connected to iron, thermogravimetric analysis confirmed the presence of water molecules located within the channels. The investigation of the electron density within the cavities revealed four water molecules present within the cavities of FeFFIVEH$_2$O-1-Ni. A hydrogen bond network between fluorine atoms of pillars and water guest molecules was revealed with the four water molecules forming a cluster having a tetrahedral shape. It must be noted that water molecules from the pillar are also part of the network.

What is claimed is:

1. A metal organic framework, comprising:
   a pillar characterized by the formula ($M_bF_5(O/H_2O)$), where $M_b$ is an element from periodic groups IIIA, IIIB, IVB, VB, VIB, and VIII; and
   a square grid characterized by the formula ($M_a$(ligand)$_x$), where $M_a$ is Ni$^{2+}$, ligand is pyrazine, and x is 2;
   wherein pillaring of the square grids with the pillars forms a metal-organic framework.

2. The metal organic framework of claim 1, wherein $M_b$ comprises Al$^{+3}$, Ga$^{3+}$, Fe$^{+2}$, Fe$^{+3}$, Cr$^{2+}$, Cr$^{3+}$, Ti$^{3+}$, V$^{3+}$, V$^{5+}$, Sc$^{3+}$, In$^{3+}$, Nb$^{5+}$, or Y$^{3+}$.

3. The metal organic framework of claim 1, wherein the pillar is (NbOF$_5$)$^{2-}$, (AlF$_5$(H$_2$O))$^{2-}$, or (FeF$_5$(H$_2$O))$^{2-}$.

4. The metal organic framework of claim 1, wherein the pillar is (NbOF$_5$)$^{2-}$, wherein the metal organic framework includes a double-bonded oxygen in a confined space.

5. The metal organic framework of claim 1, wherein the metal organic framework includes open metal sites in a confined space.

6. The metal organic framework of claim 1, wherein the metal organic framework is stable in the presence of water and H$_2$S.

7. The metal organic framework of claim 1, wherein the metal organic framework includes one or more open metal sites.

8. The metal organic framework of claim 1, wherein a pore size of the metal organic framework ranges from about 2.8 Å to about 4.8 Å.

9. The metal organic framework of claim 1, wherein a specific surface area of the metal organic framework ranges from about 250 m$^2$/g to about 500 m$^2$/g.

10. The metal organic framework of claim 1, wherein a pore volume of the metal organic framework ranges from about 0.1 cm$^3$/g to about 0.25 cm$^3$/g.

11. A method of fabricating a metal organic framework, the method comprising:
    combining a fluorhydric acid solution, a Ni$^{2+}$ source, a second metal source, and a solvent, sufficient to form a mixture;
    reacting the mixture over a period of time sufficient to form a reacted mixture;
    processing the reacted mixture to provide a metal organic framework via pillaring of square grids with a pillar, wherein the pillar is characterized by the formula ($M_bF_5(O/H_2O)$), where $M_b$ is an element from periodic groups IIIA, IIIB, IVB, VB, VIB, and VIII, and the square grids are characterized by the formula ($M_a$(ligand)$_x$), where $M_a$ is Ni$^{2+}$; ligand is pyrazine, and x is 2.

12. The method of claim 11, wherein the second metal source comprises an Al$^{+3}$ source, an Fe$^{+2}$ source, an Fe$^{+3}$ source, a Cr$^{2+}$ source, a Cr$^{3+}$ source, a Ti$^{3+}$ source, a V$^{3+}$ source, a V$^{5+}$ source, a Sc$^{3+}$ source, an In$^{3+}$ source, a Nb$^{5+}$ source, or a Y$^{3+}$ source.

13. The method of claim 11, wherein the solvent comprises one or more of water, ethanol, methanol, dimethylformamide, and diethylformamide.

14. The method of claim 11, wherein reacting the mixture comprises heating the mixture to a temperature between about 80° C. to about 200° C.

15. The method of claim 11, wherein processing the reacted mixture comprises one or more of filtering, rinsing with water, and removing excess reactants.

16. The method of claim 11, further comprising evacuating guest molecules from the metal organic framework to create open metal sites.

17. The method of claim 11, wherein the Ni$^{2+}$ source is nickel nitrate, hydrated nickel nitrate, nickel chloride, hydrated nickel chloride, nickel fluoride, hydrated nickel fluoride, nickel oxide, or hydrated nickel oxide.

18. The method of claim 11, wherein the pillar is (NbOF$_5$)$^{2-}$, (AlF$_5$(H$_2$O))$^{2-}$, or (FeF$_5$(H$_2$O))$^{2-}$.

19. The method of claim 11, wherein the pillar is (NbOF$_5$)$^{2-}$, wherein the metal organic framework includes a double-bonded oxygen in a confined space.

20. The method of claim 11, wherein $M_b$ comprises Al$^{+3}$, Ga$^{3+}$, Fe$^{+2}$, Fe$^{+3}$, Cr$^{2+}$, Cr$^{3+}$, Ti$^{3+}$, V$^{3+}$, V$^{5+}$, Sc$^{3+}$, In$^{3+}$, Nb$^{5+}$, or Y$^{3+}$.

* * * * *